United States Patent [19]

Hüttinger et al.

[11] Patent Number: 4,698,178

[45] Date of Patent: Oct. 6, 1987

[54] USE OF POLYOXYALKYLENE-POLYSILOXANE COPOLYMERS WITH SILICON-LINKED, LONG-CHAIN ALKYL RADICALS AS EMULSIFIERS FOR THE PREPARATION OF WATER/OIL EMULSIONS

[75] Inventors: Rudolf Hüttinger; Hans-Joachim Kollmeier, both of Essen; Rolf-Dieter Langenhagen, Hattingen-Niederwenigern; Alfred Walter; Wilhelm Wolfes, both of Essen, all of Fed. Rep. of Germany

[73] Assignee: Th. Goldschmidt AG, Essen, Fed. Rep. of Germany

[21] Appl. No.: 777,593

[22] Filed: Sep. 19, 1985

[30] Foreign Application Priority Data

Oct. 3, 1984 [DE] Fed. Rep. of Germany ....... 3436177

[51] Int. Cl.$^4$ .................... B01J 13/00; B01F 17/04
[52] U.S. Cl. .................... 252/309; 252/314; 252/351; 252/DIG. 1; 106/287.14
[58] Field of Search ......... 252/309, 314, 351, DIG. 1; 106/287.14; 556/446

[56] References Cited

U.S. PATENT DOCUMENTS

| | | | |
|---|---|---|---|
| 4,011,168 | 3/1977 | Uhlmann | 252/63.7 |
| 4,047,958 | 9/1977 | Yoneyama | 96/87 R |
| 4,268,499 | 5/1981 | Keil | 424/68 |
| 4,356,098 | 10/1982 | Chagnon | 252/309 |
| 4,381,241 | 4/1983 | Romenesko | 252/8.5 P |
| 4,421,656 | 12/1983 | Donatelli | 252/351 |

Primary Examiner—John F. Terapane
Assistant Examiner—Catherine S. Kilby
Attorney, Agent, or Firm—Toren, McGeady & Associates

[57] ABSTRACT

The invention relates to the use of copolymers of the average formula

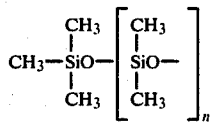

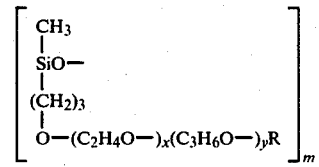

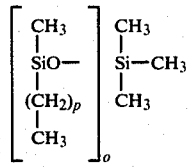

in which
R is an alkyl radical with 1 to 4 carbon atoms or a hydrogen radical;
n = 10 to 200;
m = 1 to 25;
o = 1 to 100 with the proviso that o is not less than m, and 3 o is less than n in the average molecule;
p = 7 to 17; and wherein the molecular weight of the $(C_2H_4O-)_x(C_3H_6O-)_yR$ radical is 250 to 2,000 with x and y being selected so that the weight ratio of oxyethylene to oxypropylene is 100:0 to 20:80, as emulsifiers for the preparation of W/O emulsions, whose oily phase consists of or contains silicone oil.

3 Claims, No Drawings

USE OF POLYOXYALKYLENE-POLYSILOXANE COPOLYMERS WITH SILICON-LINKED, LONG-CHAIN ALKYL RADICALS AS EMULSIFIERS FOR THE PREPARATION OF WATER/OIL EMULSIONS

BACKGROUND OF THE INVENTION

1. Field of the Invention

The invention relates to the use of known copolymers, based on polysiloxanes, as emulsifiers for the preparation of W/O (water/oil) emulsions, whose oily phase consists of or contains silicone oil.

2. Description of the Prior Art

For the preparation of emulsions of the W/O type, emulsifiers are used which preferably are soluble or dispersible in oil and whose HLB value generally is less than 8. Such emulsifiers are normally used in an amount of 10 to 20 weight percent, based on the weight of the oily phase. Examples of such W/O emulsifiers include the fatty acid esters of glycerin, polyglycerin, sorbitol or wool wax alcohols. As the fatty acid component, oleic acid or isostearic acid is generally used.

These W/O emulsions are preferred for use in cosmetics and pharmacy, but are also used for technical purposes.

According to the state of the art, special difficulties arise in the preparation of water/oil emulsions whose oily phase consists partly or completely of silicone oil. Conventional emulsifiers based on polyol esters of fatty acids do not produce satisfactory emulsions with silicone oils. Special formulations have to be worked out in each case for particular problems.

For example, U.S. Pat. No. 4,268,499, page 1, line 6, discloses antiperspirant preparations in the form of W/O emulsions which consist of:

(a) 30–60 parts by weight of an aqueous solution of an astringent, e.g., aluminum chloride, as a discontinuous phase;

(b) 27–67.5 parts by weight of a volatile liquid with a boiling point below 250° C., e.g., a cyclic dimethylsiloxane;

(c) 0.5–3 parts by weight of a W/O emulsifier with an HLB value of 2 to 10;

(d) 1–5 parts by weight polyoxyalkylene-polysiloxane copolymer; and (e) 1–5 parts by weight of an O/W emulsifier with an HLB value of 11 to 17;

wherein components (a) to (e) add up to 100 parts by weight.

Furthermore, for the preparation of W/O emulsions whose oily phase consists of silicone oil or contains this oil in a predominant amount, emulsifiers are commercially obtainable which consist of a solution of polyoxyalkylene-polysiloxane copolymers in a cyclic siloxane. These products are obtainable, for example, under the name of DOW CORNING Q2-3225C. Their use is described in the brochure "A Formulary of Product Application in Skin Care by DOW CORNING".

These products are, however, not satisfactory in all respects. The W/O preparations must be storage stable in order to ensure an adequate shelf life and a constant product quality. The emulsions must maintain a constant consistency over a period of several months, and neither oil nor water may separate out. This storage stability must, moreover be maintained at temperatures ranging from −5° C. to +40° C. There are, however, still particular difficulties with preparing stable W/O emulsions having silicone oils as the oily, continuous phase, wherein the silicone content is higher than 20 weight percent and preferably, higher than 30 weight percent, based on the total weight of the emulsion, and/or which contain, in addition to the silicone oil, other oily substances, such as, paraffin oils, ester oils or liquid or solid waxes, such as, vegetable, animal or mineral waxes. The W/O emulsions prepared from such mixtures of silicone oil and carbon-based organic oils using emulsifiers of the state of the art, generally show inadequate emulsion stability and break within hours or days. Even the preparation of a briefly stable emulsion is frequently impossible.

Copolymers are known in which polyoxyalkylene groups, as well as long-chain hydrocarbon groups are linked to a linear polysiloxane. The synthesis of such compounds is described in U.S. Pat. Nos. 3,234,252, 4,047,958, 4,427,958, 3,427,271 and 2,846,458. The synthesis is preferably accomplished by adding an olefin with, for example, 6 to 18 carbon atoms, and a polyoxyalkylene ether of an olefinically unsaturated alcohol, e.g., the polyoxyalkylene ether of allyl alcohol, to a polydiorganosiloxane having SiH groups, the addition being carried out in the presence of a catalyst containing platinum.

According to U.S. Pat. No. 4,381,241, these copolymers can be used as emulsifiers for the preparation of W/O emulsion of salt solutions in liquid hydrocarbons, which can be used as drilling liquids. There is no indication, however, that such compounds could be suitable for the preparation of W/O emulsions, the oily phase of which consists of silicone oil and, optionally, of other carbon-based organic oils or waxes.

SUMMARY OF THE INVENTION

We have discovered a method for preparing water-/oil emulsions wherein the oily phase consists of or contains silicone oil, and wherein the minimum amount of emulsifier is required. The emulsions have a high stability and maintain this stability even if the temperature changes. The emulsifiers are also physiologically safe, since the preferred area of application of the W/O emulsion is in cosmetics and pharmacy.

More particularly, this is accomplished by using, as an emulsifier for the preparation of W/O emulsions whose oily phase consists of or contains silicone oil, copolymers having the average formula:

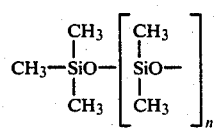

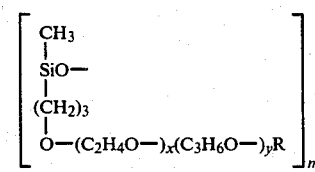

-continued

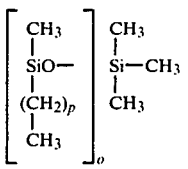

in which
R is an alkyl radical with 1 to 4 carbon atoms or a hydrogen radical;
n=10 to 200;
m=1 to 25;
o=1 to 100 with the proviso that o is not less than m, and 3 o is less than n in the average molecule;
p=7 to 17;
and wherein the molecular weight of the $(C_2H_4O-)_x(C_3H_6O-)_yR$ radical is 250 to 2,000 with x and y being selected so that the weight ratio of oxyethylene to oxypropylene is 100:0 to 20:80.

The amount of copolymer used is from 0.3 to 5 weight percent, based on the total weight of the emulsion.

DESCRIPTION OF THE PREFERRED EMBODIMENT

Preferably, R is a methyl or a hydrogen radical. Especially preferred are copolymers of Formula I, in which R is a hydrogen radical, n=25 to 150, o=5 to 50, m=1 to 15, o being not less than 2 m and 3 o being less than n. The preferred weight ratio of oxyethylene to oxypropylene groups is 40:60 to 70:30. The molecular weight of the $(C_2H_4O-)_x(C_3H_6O-)_yR$ radical is 400 to 1,200.

The oxyethylene and oxypropylene units may be distributed statistically or arranged in blocks.

The copolymers are used preferably in amounts of 0.5 to 2 weight percent, based on the total weight of the emulsion.

An essential characteristic of the copolymers for use in accordance with the invention is that one or more long-chain alkyl radicals, as well as one or more polyoxyalkylene radicals of a particular composition, linked to the backbone by an SiC bond, are present next to each other in the average molecule. Moreover, the number of polyoxyalkylene radicals may, at the outside, be equal to the number of units having long-chain alkyl radicals. Preferably, the number of units with long-chain alkyl radicals is at least twice as large as the number of units with oxyalkylene radicals. By these means it is ensured that the ratio of hydrophilic to hydrophobic portions in the molecule is so balanced that an optimum W/O emulsion stability is achieved.

The condition that the number of dimethylsiloxy units must be larger than three times the number of siloxy units which carry long-chain alkyl radicals, is of essential importance for the compatibility of the compounds of Formula I with the silicone oil, which is a component of the continuous phase of the emulsion. The emulisifers of Formula I differ in this respect significantly from the emulsifiers disclosed in European Patent Application No. 0 125 779 wherein the number of dimethylsiloxy units is equal to or less than three times the number of siloxy units with long-chain alkyl radicals. Emulsifiers which satisfy this condition exhibit only slight compatibility with silicone oils and are significantly less suitable for the preparation of water/oil emulsions whose oily phase contains silicone oil.

The emulsifiers for use according to the invention may also be used in combination with known W/O emulsifiers, especially esters of polyols and fatty acids, such as, for example, glycerol, polyglycerol, sorbitol or wool wax alcohol oleates or isostearates. Those skilled in the art know that emulsifier mixtures frequently enable particularly stable emulsions to be prepared. In accordance with the invention, an appropriate weight ratio of copolymers to fatty acid esters is about 1:0.5 to 1:2.

The continuous oily phase may consist exclusively of silicone oils. Within the meaning of the present invention, silicone oils are liquid to very viscous, particularly linear or cyclic, organosilicon compounds, whose silicon units are predominantly difunctional and correspond to the formula

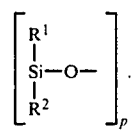

The $R^1$ and $R^2$ radicals may be the same or different and are hydrocarbon radicals, especially alkyl or aryl radicals, with methyl or phenyl radicals being especially preferred. A portion of the $R^1$ and $R^2$ radicals may be hydrogen radicals; p is number not less than 2. The silicone oils may have an end group and especially may be groups having the formula $(R^1, R^2)_3SiO-$ or hydroxyl groups. Trifunctional silicon units of formula $(R^1, R^2)SiO_{1.5}-$ may also be contained in small amounts. The viscosity of the silicones usually falls within the range of 0.5 mPa×sec. to $3\times10^5$ mPa×sec.

The oily phase of the W/O emulsions may contain carbon based organic oils or waxes in addition to the silicone oil. As carbon based organic oils, especially mineral oils and animal or vegetable oils may be used. Examples of these oils are paraffin oils of different viscosities, fish oils, neat's foot oils, bone oils, mink oil, olive oil, castor oil, peanut oil, and palm oil. Furthermore suitable are liquid waxes, such as, jojoba oil, or synthetic oils, such as, isopropyl myristate, isopropyl stearate, hexyl laurate or oleyl oleate.

Fats or waxes having a melting point or melting region below 100° C., may also be added to the oils to be emulsified.

To increase the stability of the emulsion at low temperatures, polyols, such as, glycerin, 1,2-propylene glycol or sobirtol may be added in a known manner in amounts of 0.5 to 15 weight percent, based on the total weight.

The stability at elevated temperatures can be improved in a known manner by the addition of electrolytes, such as, sodium chloride or magnesium sulfate, or by the addition of metal soaps, such as, calcium or aluminum stearate.

The oily continuous phase content of the emulsion can vary within wide limits. It amounts to 8 to 50 weight percent of the total weight of the preparation.

The preparation of the desired W/O emulsion is accomplished in a known manner. Advisably, the emulsifier or emulsifier mixture is dissolved or dispersed in the oily phase. If the latter contains portions of higher melting materials, such s, beeswax, it is heated above the melting range of these components. The water is then added to the oily phase with thorough stirring. Further components of the emulsion, such as, preservatives, perfumes, dyes or stabilizers, are generally added to the phase in which they are soluble or easily dispersible.

The W/O emulsions obtained with the copolymers of the present invention have the required high stability and maintain this over a wide temperature range and at relatively low emulsifier concentrations. As a result of the low emulsifier content, the properties of the oily phase are accordingly only slightly affected by the emulsifier. This is particularly important for cosmetic or pharmaceutical applications. The W/O emulsions prepared with the inventive emulsifiers are also suitable for technical purposes, for example, for use as preservatives and polishes for furniture, lacquered metal or floors.

The following examples (as set forth in the Tables) illustrate the compositions of emulsions with the inventive copolymers, the preparation of these emulsions and their properties.

started, water in which salt and, optionally, glycerin or propylene glycol are dissolved, is added to the mixture of emulsifier and oil. The W/O emulsion obtained is stirred until it reaches room temperature.

We claim:

1. An emulsion prepared by the method comprising preparation of a water/oil emulsion wherein the oily phase is or contains silicone oil by mixing the oily phase with water in the presence of an emulsifier, the improvement which comprises said emulsifier being present in an emulsifying effective amount and being a copolymer having the average formula:

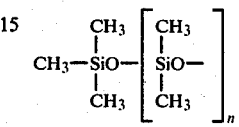

| COMPOSITION OF THE EMULSIONS | | | | | | | | |
|---|---|---|---|---|---|---|---|---|
| Emulsion/Components | 1 Wt. % | 2 Wt. % | 3 Wt. % | 4 Wt. % | 5 Wt. % | 6 Wt. % | 7 Wt. % | 8 Wt. % |
| A | | | | | | | | |
| Emulsifier I | 1.0 | — | — | — | — | — | — | — |
| Emulsifier II | — | 1.0 | — | — | — | — | — | — |
| Emulsifier III | — | — | 1.0 | — | — | — | — | — |
| Emulsifier IV | — | — | — | 1.0 | — | — | — | — |
| Emulsifier V | — | — | — | — | 1.0 | — | — | — |
| Emulsifier VI | — | — | — | — | — | 1.0 | — | — |
| Triglycerol trioleate | 0.5 | 0.5 | 0.5 | 0.5 | 0.5 | 0.5 | — | 0.5 |
| Octamethylcyclo-tetrasiloxane | 8.5 | 8.5 | 0.5 | 8.5 | 8.5 | 8.5 | 8.5 | 30.0 |
| Isopropyl myristate | 6.0 | 4.0 | 7.0 | 4.0 | 4.0 | 11.0 | 6.0 | — |
| Paraffin oil DAB 8 | 5.0 | — | 6.0 | — | — | 6.0 | 5.0 | — |
| Liquid ester wax | 2.0 | — | 5.5 | — | — | — | 2.0 | — |
| Vaseline DAB 8 | — | 5.0 | — | — | — | — | — | — |
| Micro wax | — | 0 | 2.0 | — | — | 2.0 | — | — |
| Polysiloxane-polyoxy-alkylene copolymer | — | — | — | 5.0 | 5.0 | — | — | 5.0 |
| Corn germ oil | — | — | — | — | 2.0 | — | — | — |
| 3-(4-methyl-benzylidene camphor | — | — | — | — | — | 3.0 | — | — |
| B | | | | | | | | |
| Water | 70.0 | 79.0 | 75.5 | 79.0 | 72.0 | 66.0 | 70.5 | 56.5 |
| NaCl | 2.0 | 2.0 | 2.0 | 2.0 | 2.0 | 2.0 | 2.0 | 2.0 |
| Glycerin | 5.0 | — | — | — | — | — | 5.0 | 5.0 |
| 1,2-propylene glycol | — | — | — | — | 5.0 | — | — | — |
| | 100.00 | 100.0 | 100.0 | 100.0 | 100.0 | 100.0 | 100.0 | 100.0 |

| | COMPOSITION OF EMULSIFIERS I-VI | | | | | |
|---|---|---|---|---|---|---|
| | Indices in Formula I | | | | $(C_2H_4O-)_x(C_3H_6O-)_yR$ | |
| | n | m | o | p | R | Molecular Weight | Weight Ratio $C_2H_4O:C_3H_6O$ |
| Emulsifier I | 38 | 3 | 7 | 17 | H | 490 | 20:80 |
| Emulsifier II | 73 | 4 | 21 | 15 | H | 600 | 60:40 |
| Emulsifier III | 92 | 5 | 26 | 15 | H | 550 | 60:40 |
| Emulsifier IV | 148 | 8 | 42 | 11 | H | 400 | 60:40 |
| Emulsifier V | 73 | 4 | 21 | 11 | H | 1200 | 80:20 |
| Emulsifier VI | 80 | 3 | 18 | 17 | $CH_3$ | 700 | 100:0 |

Emulsions 1 to 5, 7 and 8 have a cream-like consistency and emulsion 6 is liquid. The emulsions obtained are stable during an observation period of 3 months at 20° C. and 45° C. The stability of the emulsions cooled to −25° C. and then heated to 20° C. is not impaired. The emulsions can be spread well on the skin and are absorbed well.

The emulsions are prepared in a glass vessel, which is equipped with a stirrer. Components A are added to the vessel and melted, if necessary. After the stirrer is

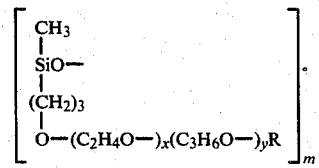

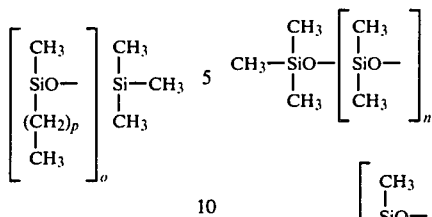

in which
R is an alkyl adical with 1 to 4 carbon atoms or a hydrogen radical;
n = 10 to 200;
m = 1 to 25;
o = 1 to 100 with the proviso that o is not less than m, and 3 o is less than n in the average molecule;
p = 7 to 17; and wherein the molecular weight of the $(C_2H_4O-)_x(C_3H_6O-)_yR$ radical is 250 to 2,000 with x and y being selected so that the weight ratio of oxyethylene to oxyethylene to oxypropylene is 100:0 to 20:80.

2. An emulsion prepared by the method as in claim 1 wherein the copolymer is present in an amount from 0.3 to 5 weight percent based on the total weight of the emulsion.

3. An emulsifier for the preparation of a water/oil emulsion wherein the oily phase is or contains silicone oil comprising

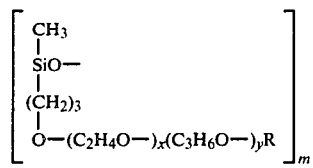

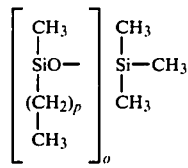

in which
R is an alkyl radical with 1 to 4 carbon atoms or a hydrogen radical;
n = 10 to 200;
m = 1 to 25;
o = 1 to 100 with the proviso that o is not less than m, and 3 o is less than n in the average molecule;
p = 7 to 17; and
wherein the molecular weight of the $(C_2H_4O-)_x(C_3H_6O-)_yR$ radical is 250 to 2,000 with x and y being selected so that the weight ratio of oxyethylene to oxypropylene is 100:0 to 20:80.

* * * * *